(12) United States Patent
Nishizono

(10) Patent No.: US 6,450,035 B1
(45) Date of Patent: Sep. 17, 2002

(54) APPARATUS AND METHOD FOR MEASURING A DEFECT OF A SAMPLE

(75) Inventor: Shigeo Nishizono, Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 50 days.

(21) Appl. No.: 09/692,201

(22) Filed: Oct. 20, 2000

(30) Foreign Application Priority Data

Feb. 25, 2000 (JP) ........................................ 2000-048663

(51) Int. Cl.⁷ .............................................. G01N 29/00
(52) U.S. Cl. ............................ 73/579; 73/1.82; 73/661
(58) Field of Search ......................... 73/579, 661, 599, 73/600, 602, 1.82, 598, 593, 591

(56) References Cited

U.S. PATENT DOCUMENTS

| | | | | |
|---|---|---|---|---|
| 3,842,663 A | * | 10/1974 | Harting et al. ................. | 73/593 |
| 4,016,752 A | * | 4/1977 | Carey ........................... | 73/652 |
| 4,478,082 A | * | 10/1984 | Sato et al. ..................... | 73/593 |
| 4,680,969 A | * | 7/1987 | Hama et al. ................... | 73/661 |
| 4,907,456 A | * | 3/1990 | Rozelle ......................... | 73/660 |
| 6,105,432 A | * | 8/2000 | Taniguchi et al. ............. | 73/649 |

* cited by examiner

*Primary Examiner*—Hezron Williams
*Assistant Examiner*—Jacques Saint-Surin
(74) *Attorney, Agent, or Firm*—Leydig, Voit & Mayer, Ltd

(57) ABSTRACT

An apparatus includes an inspection jig having a sample mounting fixture for mounting a sample, a vibrator for applying a vibration to the sample, and a sound collector for collecting vibration sound when the vibration is applied to the sample, and a sound detector for frequency analysis of the vibration sound collected by the sound collector. The sample is pinched and fixed by a contact surface of the sound collector and a fixing part with a contact area similar to the contact surface when the sample is mounted in the sample mounting fixture. The sample mounting fixture is mounted on a shaft of an inspection jig fixed in a bearing.

12 Claims, 8 Drawing Sheets

APPLIED POINT

NON-DEFECTIVE ARTICLE

WAVEFORM VIBRATES IN MINUS REGION

DEFECTIVE ARTICLE

WAVEFORM VIBRATES IN PLUS REGION

DEFECTIVE ARTICLE

WAVEFORM VIBRATES IN PLUS AND MINUS REGIONS

APPARATUS AND METHOD FOR MEASURING A DEFECT OF A SAMPLE

BACKGROUND OF THE INVENTION

1. Field of the Invention

This invention relates to an apparatus for measuring defects such as substrate fractures or internal cracks in relation to samples such as material substrates (photo-voltaic cell, polycrystalline silicon substrate), and particularly to a measuring apparatus for improving reproducibility of measuring operations and operating efficiency and improving accuracy of defect determination while doing little damage to the sample.

2. Description of the Related Art

Conventionally, there is an apparatus disclosed in, for example, JP-A-7-113791 as a measuring apparatus for speedily objectively evaluating uniformity of samples without doing damage to samples such as material substrates.

FIG. 9 is a block diagram showing a uniformity measuring apparatus of the samples. This measuring apparatus comprises a vibrator 102 for applying vibration to the end of a flat plate sample 101, a first vibration sensor 103 which is spaced a predetermined distance away from the applied vibration portion of the vibrator 102 and detects the vibration transferring the sample 101, and a second vibration sensor 104 which is spaced a predetermined distance away from the vibration sensor 103 and detects the vibration transferring to the sample 101.

The vibration applied by the vibrator 102 is transferred from the applied vibration portion of the sample 101 to the other end direction and is detected by the first and second vibration sensors 103 and 104. Vibration detection signals detected by the first and second vibration sensors 103 and 104, respectively, are fed to filters 105 and 106 for eliminating noise signals and selecting a signal with a predetermined frequency, and are amplified by amplifiers 107 and 108. The detection signal from the vibration sensor 103 is fed to a terminal of a channel 1 of an oscilloscope 109 and the detection signal from the second vibration sensor 104 is fed to a terminal of a channel 2 of the oscilloscope 109 and the detection signals are respectively displayed. Then, uniformity of the sample 101 can be evaluated by calculating a difference in vibration transfer time or a difference in transfer speed based on each of the detection signals displayed on the oscilloscope 109.

In the conventional apparatus described above, however, a fixing method of the sample 101, a positioning method of the sample 101 and the vibrator 102, and an applied vibration point of the vibrator 102 to the sample 101 were not disclosed at all. On the contrary, depending on determination of the fixing method, the positioning method and the applied vibration point described above, there was the possibility of causing damage to the sample due to the applied vibration, a decrease in detection accuracy of defect measurement and a decrease in operating efficiency.

SUMMARY OF THE INVENTION

The invention is implemented to solve such problems, and it is an object of the invention to provide an apparatus for measuring defects of a sample capable of improving mounting operations of the sample or a vibrator and improving accuracy of defect measurement and making an objective evaluation without doing damage to the sample.

According to a first aspect of the invention, there is provided an apparatus for measuring defects of a sample, comprising an inspection jig including a sample mounting portion for mounting the sample, a vibrator for applying vibration to the sample, and a sound collector for collecting a vibration sound when the vibration is applied to the sample by this vibrator; and a sound detector for conducting frequency analysis of the vibration sound collected by the sound collector, and the sample is pinched and fixed by a contact surface of the sound collector and a fixing part with a contact area similar to this contact surface when the sample is mounted in the sample mounting portion.

According to a second aspect of the invention, there is provided an apparatus for measuring defects of a sample, comprising an inspection jig including a sample mounting portion for mounting the sample, a vibrator for applying vibration to the sample, and a sound collector for collecting a vibration sound when the vibration is applied to the sample by this vibrator; and a sound detector for conducting frequency analysis of the vibration sound collected by the sound collector, and a fixing part for fixing the sample in the sample mounting portion is made of a cushioning material and the sample mounting portion is made movable in relation to an applied vibration direction of the sample.

According to a third aspect of the invention, there is provided an apparatus for measuring defects of a sample, comprising an inspection jig including a sample mounting portion for mounting the sample, a vibrator for applying vibration to the sample, and a sound collector for collecting a vibration sound when the vibration is applied to the sample by this vibrator; and a sound detector for conducting frequency analysis of the vibration sound collected by the sound collector, and the sample is resiliently pinched and fixed by the sound collector of the sample mounting portion and a fixing part.

In the invention, a surface having small unevenness of the sample is set to the contact side of the sound collector of the sample mounting portion.

In the invention, an applied point of the vibrator is set to a surface which is in the vicinity of the center of the sample and has no unevenness.

In the invention, a jig for keeping impact force and a release point of the vibrator constant is provided.

According to a fourth aspect of the invention, there is provided a method for measuring defects of a sample, comprising the steps of pinching and fixing the sample by a contact surface of a sound collector of a sample mounting portion and a fixing part with a contact area similar to this contact surface, applying vibration to the sample fixed in the sample mounting portion by a vibrator, collecting a vibration sound when the vibration is applied to the sample on the time series by the sound collector, and conducting frequency analysis of the vibration sound collected by the sound collector.

According to a fifth aspect of the invention, there is provided a method for measuring defects of a sample, comprising the steps of pinching and fixing the sample by a sound collector of a sample mounting portion movable in relation to an applied vibration direction of the sample and a fixing part made of a cushioning material, applying vibration to the sample fixed in the sample mounting portion by a vibrator, collecting a vibration sound when the vibration is applied to the sample on the time series by the sound collector, and conducting frequency analysis of the vibration sound collected by the sound collector.

According to a sixth aspect of the invention, there is provided a method for measuring defects of a sample, comprising the steps of resiliently pinching and fixing the sample by a sound collector of a sample mounting portion and a fixing part, applying vibration to the sample fixed in the sample mounting portion by a vibrator, collecting a vibration sound when the vibration is applied to the sample on the time series by the sound collector, and conducting frequency analysis of the vibration sound collected by the sound collector.

DETAILED DESCRIPTION OF THE PRESENT INVENTION

The present invention will be described in detail with reference to the accompanying drawings.

First Embodiment

Figure 1A:
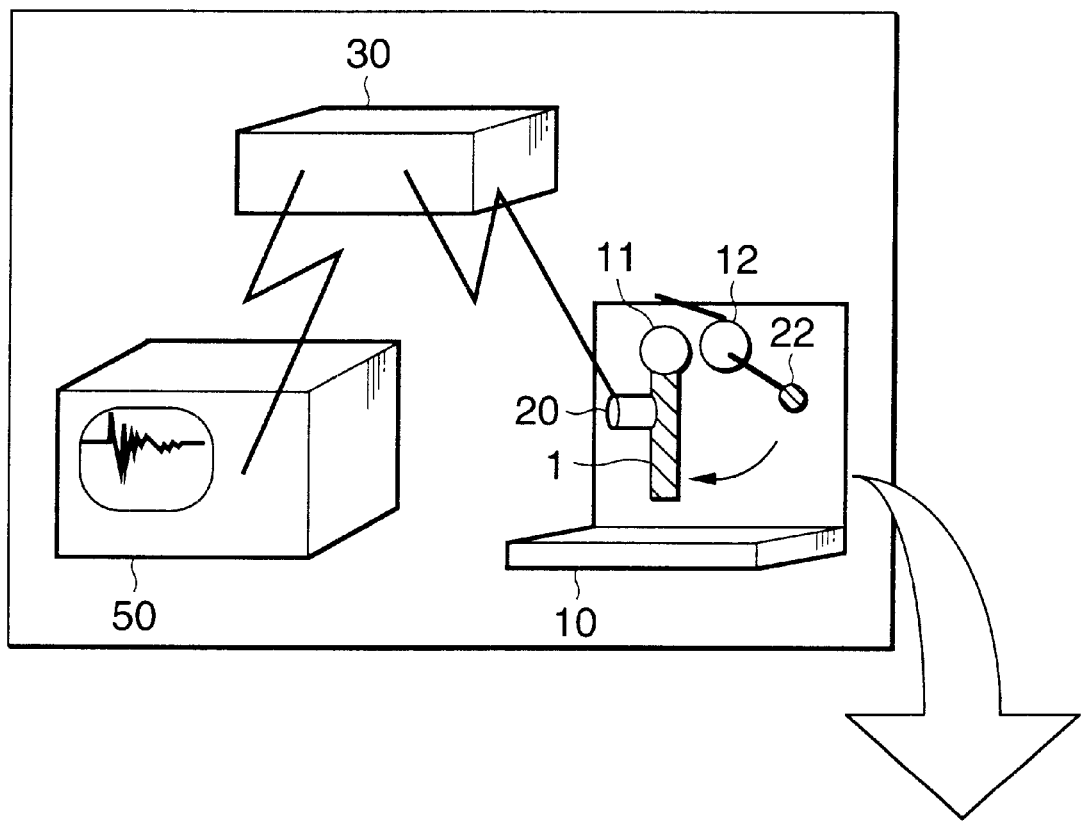
FIGS. 1A and 1B are illustrations showing an apparatus for measuring a defect of a sample according to a first embodiment of this invention.
Figure 1B:
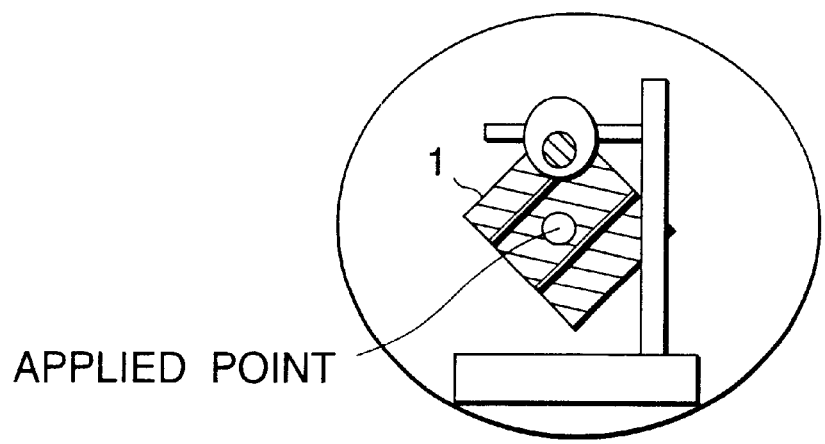

FIGS. 1A and 1B are illustrations showing an apparatus for measuring a defect of a sample according to a first embodiment of this invention. FIG. 1A is a schematic configuration view showing all of the defect measuring apparatus and FIG. 1B is a side view showing an inspection jig of the defect measuring apparatus. The defect measuring apparatus of the sample according to the first embodiment comprises an inspection jig 10 for applying vibration by a vibrator 22 with a sample 1 such as a material substrate fixed and collecting the applied vibration sound by a sound collector 20 such as a capacitor microphone, a sound detector 30 for amplifying the vibration sound collected by the sound collector 20 through an LPF (low-pass filter) and a HPF (high-pass filter) and then calculating to output it as a composite wave, and an oscilloscope 50 for displaying a waveform calculated by the sound detector 30 and determining defects of the sample by the waveform.

Figure 2:
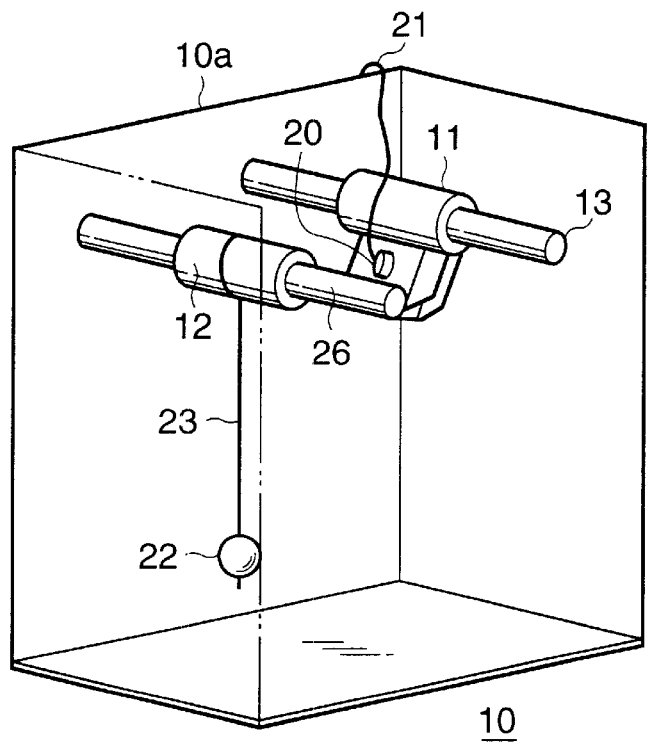
FIG. 2 is a perspective view showing the whole configuration of an inspection jig according to the first embodiment.
Figure 3:
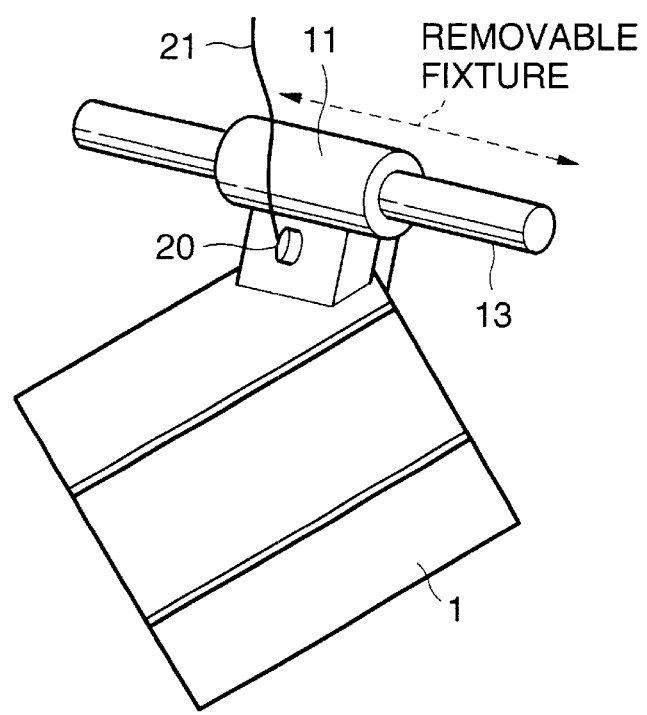
FIG. 3 is a perspective view showing a sample mounting portion of the inspection jig according to the first embodiment.

FIG. 2 is a perspective view showing the whole configuration of the inspection jig 10 of the embodiment. In FIG. 2, the inspection jig 10 mainly comprises a sample mounting portion 11 for mounting the sample 1, and a vibrator mounting part 12 for mounting the vibrator 22. As shown in FIG. 3, the sample mounting portion 11 is slidably and removably mounted on a shaft 13 provided in an inspection jig fixation side 10a through a bearing described below. Also, the vibrator mounting part 12 is slidably mounted on a shaft 26 provided in the inspection jig fixation side 10a through a bearing and mounts the vibrator 22 through a suspension wire 23 (for example, copper wire).

Figure 4:
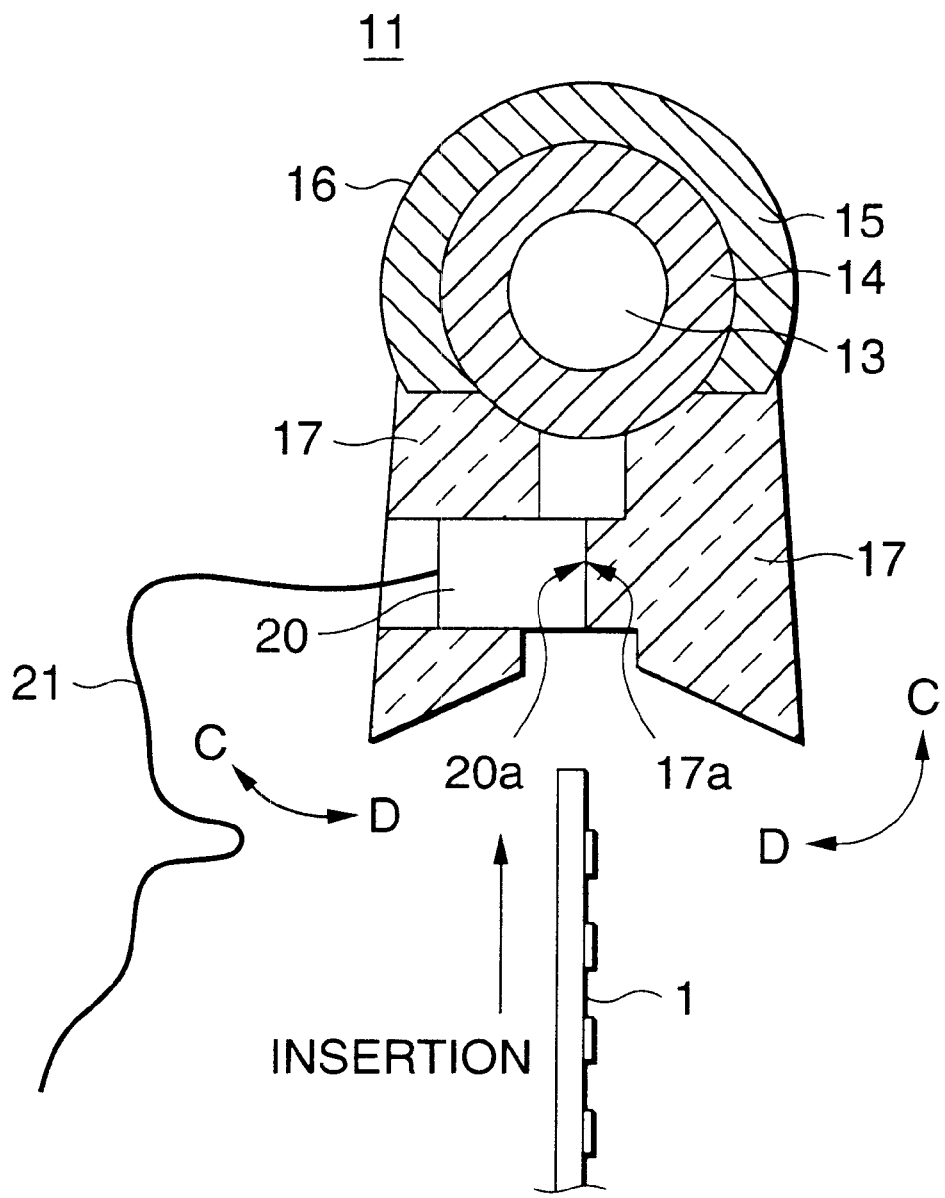
FIG. 4 is a sectional view showing the sample mounting portion of the inspection jig according to the first embodiment.

FIG. 4 is a sectional view showing details of the sample mounting portion 11 of the inspection jig 10. In FIG. 4, the sample mounting portion 11 comprises a bearing 14 slidably mounted on the shaft 13 of the inspection jig fixation side 10a, a protective part 15 provided so as to surround this bearing 14, a sample fixing part 17 for fixing the sample 1, and a metal plate 16 placed so as to covering the protective part 15 and the sample fixing part 17. Incidentally, the sample fixing part 17 preferably uses materials such as PE light having cushion effect. The sound collector 20 such as a capacitor microphone is mounted in a hole provided in a part of the sample fixing part 17. Then, the sample 1 is pinched and fixed by a contact surface 20a of the sound collector 20 and a fixing part contact surface 17a with substantially the same area as this contact surface 20a. The metal plate 16 enables the sample 1 to be inserted into the sample fixing part 17 by opening the metal plate 16 in the direction of C shown in FIG. 4 and enables the sample 1 to be stably supported in the sample fixing, part 17 by resiliently returning the metal plate 16 in the direction of D shown in FIG. 4.

Also, when the sample 1 is fixed in the sample fixing part 17, the contact surface 20a of the sound collector 20 is contacted on the surface having small unevenness of the sample 1, for example, the rear of the material substrate. As a result of this, collection of the applied vibration sound by the sound collector 20 can more be ensured to reduce a detection error.

Figure 5:
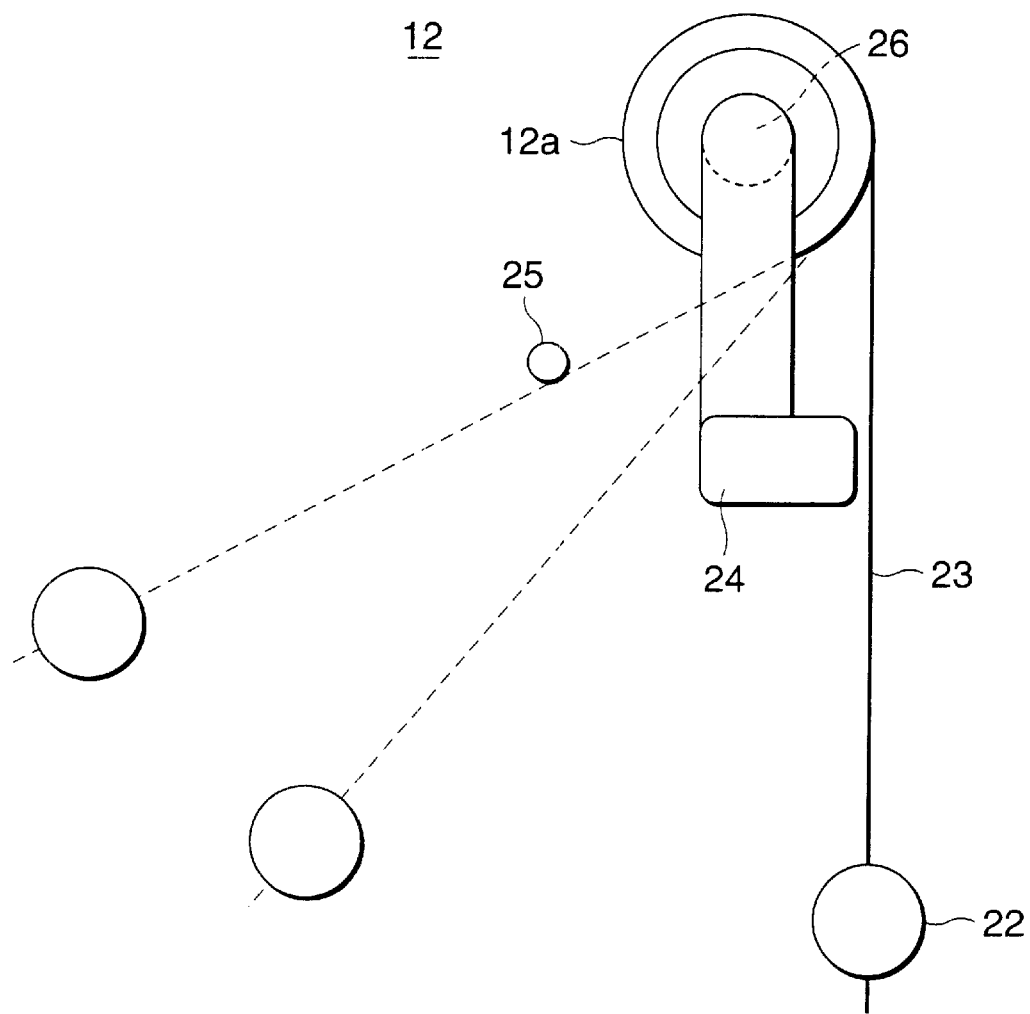
FIG. 5 is a side view showing a vibrator mounting part of the inspection jig according to the first embodiment.

FIG. 5 is a side view showing details of the vibrator mounting part 12 of the inspection jig 10. In FIG. 5, a vibrator mounting body 12a is slidably mounted on the shaft 26 provided in the inspection jig fixation side 10a through the bearing and mounts the vibrator 22 through the suspension wire 23 (for example, copper wire). A handle 24 of the vibrator mounting part 12 is means for adjusting the level of the vibrator 22 and the vibrator 22 is positioned so that the vibrator 22 collides with a predetermined applied point of the sample 1 mounted in the sample mounting portion 11. Also, a pole 25 for positioning provided in the inspection jig fixation side 10a plays a role in keeping a release point of the vibrator 22 constant.

Figure 6:
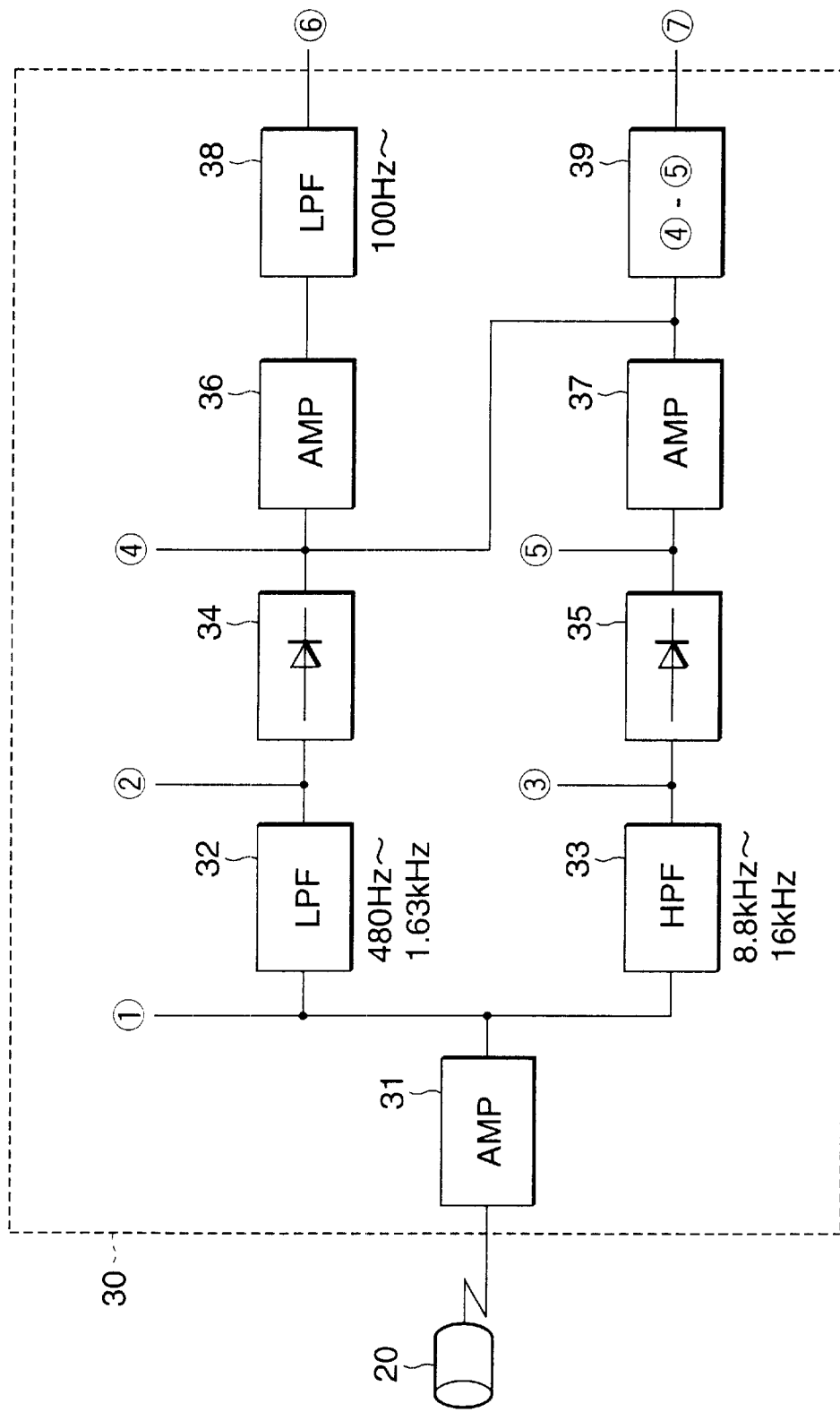
FIG. 6 is a circuit block diagram showing a sound detector according to the first embodiment.

FIG. 6 shows a circuit block diagram of the sound detector 30. The sound detector 30 sequentially collects the vibration sound collected by the sound collector 20 such as a capacitor microphone during a start of vibration to damping and convergence. That is, the vibration sound collected by the sound collector 20 is amplified by an amplifier 31, and then is fed to a low-pass filter (LPF) 32 and a high-pass filter (HPF) 33. Then, after the frequency is stratified by the LPF 32 and the HPF 33, the vibration sound is fed to rectifiers 34 and 35, respectively. After an output signal of the rectifier 34 is amplified by an amplifier 36, the signal is outputted to a terminal 6 through an LPF 38. Also, a signal amplifying an output signal of the rectifier 35 by an amplifier 37 is subtracted from the output signal of the rectifier 34 at a differential circuit 39 and the signal is outputted to a terminal 7.

A composite wave calculated by the sound detector 30 as described above is sequentially outputted to the oscilloscope 50. That is, the calculated results of the sound detector 30 are sequentially outputted to the oscilloscope 50 during a vibration start of the sample 1 to damping and convergence, and determine defects such as substrate fractures or internal cracks from a display region of the waveform.

Figure 7A:
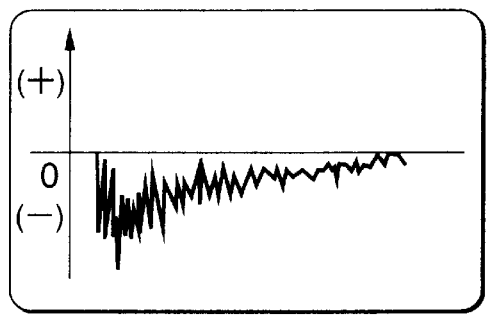
FIGS. 7A to 7C are graphs for determining defects of the sample from waveforms outputted to an oscilloscope according to the first embodiment.
Figure 7B:
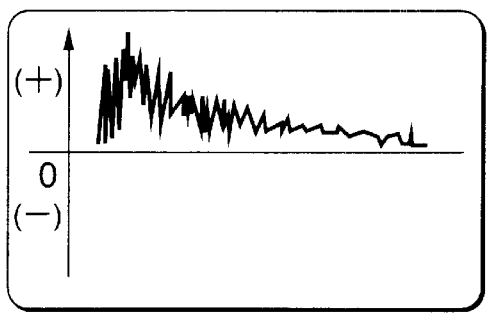
Figure 7C:
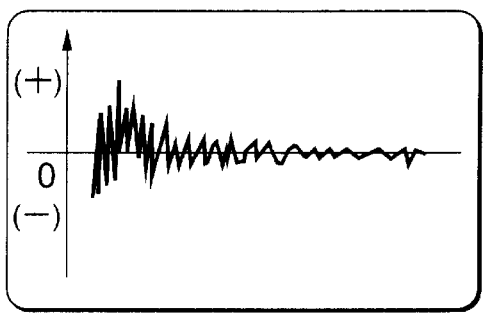

FIGS. 7A to 7C are graphs for determining defects of the sample from waveforms outputted to the oscilloscope 50. In the case of the embodiment, in a determination region of the defects of the sample, for a non-defective article (without fractures or internal cracks), the waveform vibrates to converge in only a minus region as shown in FIG. 7A. On the contrary, for a defective article (with fractures or internal cracks), the waveform vibrates to converge in only a plus region or in plus and minus regions as shown in FIGS. 7B and 7C. In this manner, calculations of the frequency are made. Incidentally, in FIGS. 7A to 7C, an axis of ordinate indicates amplitude of the composite wave and an axis of abscissa indicates time.

Figure 8:
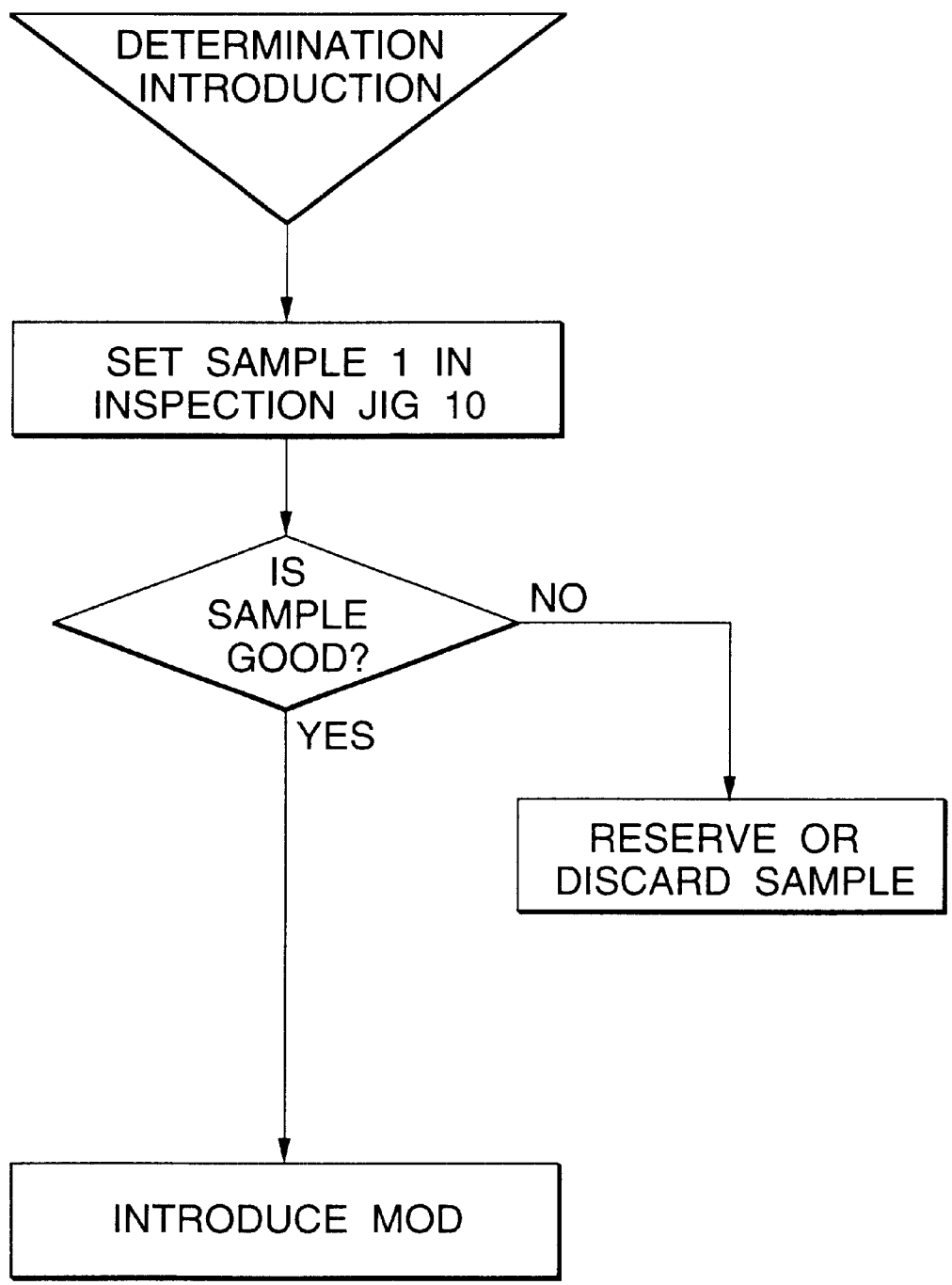
FIG. 8 is a flowchart determining the defects of the sample according to the first embodiment.
Figure 9:
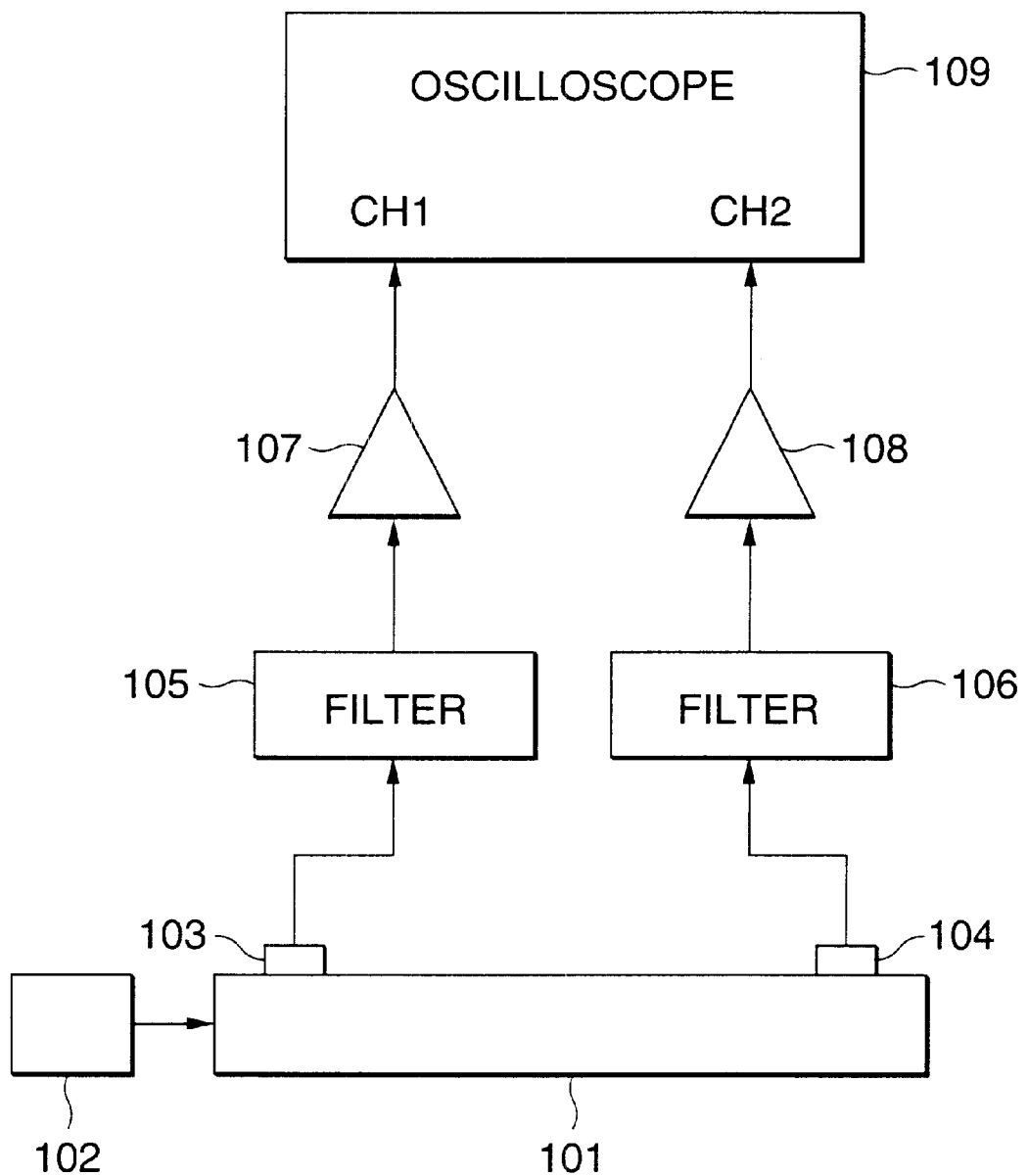
FIG. 9 is a block diagram showing a conventional uniformity measuring apparatus of a sample.

FIG. 8 is a flowchart showing operation procedure for determining the defects (fractures or internal cracks) of the sample described above. In FIG. 8, first, after the sample 1 is set in the inspection jig 10, vibration is applied to the sample 1 by the vibrator 22 and the vibration sound is collected by the sound collector 20 and is fed to the sound detector 30. In the sound detector 30, frequency analysis of the vibration sound obtained by the sound collector 20 is conducted and a composite waveform is outputted to the oscilloscope 50. An operator determines whether the sample is a non-defective article or a defective article by the graphs of the FIGS. 7A to 7C. According to the defect measuring apparatus of the sample by the invention thus, the mounting means of the sample, the mounting means of the vibrator and the technique for impacting the vibrator on the sample as described above are adopted, so that it can be determined whether the sample is the non-defective article or the defective article by the determination operation of one time.

According to the invention as described above, determination operation of defects such as fractures or internal cracks in relation to a sample such as a material substrate can be made efficient and accuracy of the defect determination can be improved and quality can be maintained without damage of the sample. Also, by improving a sample contact portion and a support portion of an inspection jig of a defect measuring apparatus of the sample of the invention, it can be determined whether the sample is a non-defective article or a defective article by the determination operation of one time.

Particularly, according to the invention, by pinching and fixing a sample by a contact surface of a sound collector and a fixing part with a contact area similar to this contact surface when the sample is mounted in a sample mounting portion, a contact area of the sample mounting portion to the sample can be reduced and detection accuracy of the defects (fractures or internal cracks) of the sample can be improved.

Also, according to the invention, a fixing part for fixing the sample in the sample mounting portion is made of a cushioning material and the sample mounting portion is mounted, for example, on a shaft of an inspection jig fixation side through a bearing, so that the sample mounting portion is designed for movable type and a shock when the vibration is applied to the sample can be minimized and damage is not caused to the sample, and effects capable of repeatedly making evaluations and determinations are obtained.

Further, according to the invention, the sample is resiliently pinched and fixed by the sound collector of the sample mounting portion and the fixing part, so that operations for setting (mounting) and resetting (removing) the sample in the sample mounting portion can be improved and the mounting operations of the sample can be semiautomated. Also, reproducibility of inspection can be improved by keeping fixed force of the sample constant.

Furthermore, according to the invention, by setting a surface having small unevenness of the sample to the contact side of the sound collector of the sample mounting portion, a detection error of an applied vibration sound can be eliminated and accuracy of defect determination can be improved.

Also, according to the invention, an applied point of the vibrator is set to a surface which is in the vicinity of the center of the sample and has no unevenness, so that the vibration can uniformly be applied to the sample and reproducibility of collected frequency can be improved.

Also, according to the invention, a jig for keeping impact force and a release point of the vibrator constant is provided, so that effects of improving reproducibility of impact (load) of the vibrator on the sample are obtained.

What is claimed is:

1. An apparatus for measuring defects of a sample, the apparatus comprising:
   an inspection jig comprising:
      an impact vibrator fort inducing vibrations in a sample;
      a sample mounting fixture for mounting the sample; and
      a sound collector mounted in the sample mounting fixture for collecting sound propagating in the sample and induced by impact of the impact vibrator, wherein the sample mounting fixture includes a movable jaw with a contact surface for resiliently clamping the sample between and in contact with the contact surface and the sound collector; and
   a sound detector for frequency analysis of the sound collected by the sound collector.

2. The apparatus according to claim 1, wherein the sound collector has a first contact area contacting the sample, and the contact surface has a second contact area substantially the same as the first contact area.

3. The apparatus according to claim 2, wherein the contact surface of the sample mounting fixture includes a cushioning material and the jaw is movable in a direction opposite a direction in which the impact vibration is applied to the sample by the impact vibrator.

4. The apparatus according to claim 1, wherein an uneven surface of the sample is placed in contact with the sound collector in the sample mounting fixture.

5. The apparatus according to claim 1, wherein an application point of the impact vibrator is proximate a center of the sample.

6. The apparatus according to claim 1, further comprising a stop for maintaining impact force and a release point of the impact vibrator constant.

7. The apparatus according to claim 1, wherein the inspection jig includes a mount with a rotatable sleeve and the impact vibrator includes a mass suspended from the sleeve by a flexible line as a pendulum for inducing vibrations in the sample by impact of the mass against the sample.

8. The apparatus according to claim 1, wherein the sound detector comprises first and second low pass filters having different frequency ranges and connected in series, receiving and processing the sound collected by the sound collector to produce a first signal for frequency analysis, and a high pass filter receiving and processing the sound collected by the sound collector to produce a second signal for frequency analysis.

9. The apparatus according to claim 8, wherein, in the sound detector, an output signal of the first low pass filter is combined with an output signal of the high pass filter to produce the second signal.

10. A method for measuring defects of a sample, the method comprising:

resiliently clamping a sample between and in contact with a sound collector and a contact area of a jaw of a sample mounting fixture;

inducing vibrations in the sample fixed in the sample mounting fixture by applying an impact to the sample;

collecting sound induced in the sample in response to the impact with the sound collector; and analyzing frequencies of the sound collected by the sound collector.

11. The method according to claim 10, wherein an area of the sound collector in contact with the sample is substantially the same as an area of the contact area of the sample mounting fixture in contact with the sample.

12. The method according to claim 11, wherein the jaw of the sample mounting fixture is movable in a direction opposite a direction of the impact applied to the sample and includes a cushioning material on the contact area.

\* \* \* \* \*